US008510124B2

(12) United States Patent
Gowdy et al.

(10) Patent No.: US 8,510,124 B2
(45) Date of Patent: Aug. 13, 2013

(54) PROVIDING TRANSPARENT HEALTH CARE INFORMATION TO CONSUMERS

(75) Inventors: Wayne Gowdy, Tolland, CT (US); Roberta Downey, Glastonbury, CT (US); Ronald A. Williams, Farmington, CT (US)

(73) Assignee: Aetna Inc., Hartford, CT (US)

( * ) Notice: Subject to any disclaimer, the term of this patent is extended or adjusted under 35 U.S.C. 154(b) by 1178 days.

(21) Appl. No.: 11/457,449

(22) Filed: Jul. 13, 2006

(65) Prior Publication Data

US 2008/0015892 A1 Jan. 17, 2008

(51) Int. Cl.
G06Q 10/00 (2012.01)
G06Q 50/00 (2012.01)

(52) U.S. Cl.
USPC .................................. 705/2; 705/3; 705/4

(58) Field of Classification Search
USPC ...................................... 705/2, 3, 4
See application file for complete search history.

(56) References Cited

U.S. PATENT DOCUMENTS

| | | | | |
|---|---|---|---|---|
| 6,735,569 | B1* | 5/2004 | Wizig | 705/4 |
| 7,818,181 | B2* | 10/2010 | Green | 705/2 |
| 2002/0147617 | A1* | 10/2002 | Schoenbaum et al. | 705/4 |
| 2003/0009355 | A1* | 1/2003 | Gupta | 705/2 |
| 2003/0093294 | A1* | 5/2003 | Passantino | 705/2 |
| 2003/0154103 | A1* | 8/2003 | Koningsberg | 705/2 |
| 2004/0039604 | A1* | 2/2004 | Tallal, Jr. | 705/2 |
| 2005/0086080 | A1 | 4/2005 | Stump et al. | |
| 2006/0080146 | A1 | 4/2006 | Cook et al. | |
| 2007/0088580 | A1* | 4/2007 | Richards, Jr. | 705/4 |

FOREIGN PATENT DOCUMENTS

WO    WO 03/032192 A1 *  4/2003

OTHER PUBLICATIONS

The Cincinnati Post, Editorial Opinion, A Worthy Experiment, Aug. 22, 2005.*
Fuhrmans, V., Patients Give New Insurance Mixed Reviews, *The Wall Street Journal*, D1, Jun. 14, 2005.
Hanft, A., "Another Look at Healthcare Marketing", *FreshInc., the Inc.Com Weblog*, Aug. 19, 2004, obtained from http://blog.inc.com/archives/2004/08/19/another_look_at_healthcare_marketing.html on Jul. 14, 2006.
Kershaw-Staley, T., "Plan to unveil prices concerns physicians", *Dayton Business Journal*, Aug. 26, 2005, obtained from http://www.bizjournals.com/dayton/stories/2005/08/29/story7.html?t=printable on Jul. 14, 2006.
Rubenstein, S., "Patients Get New Tools to Price Health Care", *The Wall Street Journal*, Jun. 13, 2006.
Rubenstein, S., "Patients Paying for Medical Care Struggle to Divine the Costs", *The Wall Street Journal Online*, Feb. 16, 2005.

(Continued)

*Primary Examiner* — Neha Patel
(74) *Attorney, Agent, or Firm* — Leydig, Voit & Mayer, Ltd

(57) ABSTRACT

Systems and methods are described for providing consumers with access to the discounted rates for health care procedures provided by primary care physicians, specialist physicians and facilities. Fee information for contracted providers is stored in a database and is accessible to consumers via an online interface. Consumers select query criteria for providers and are presented with actual cost information pertaining to procedures prospectively rendered by providers. Additional information, such as quality or efficiency of providers, can also be presented. Information on multiple providers can be obtained and presented in a comparative arrangement. The presented information can be limited to providers within a geographic region, within a cost range, within a quality range, or other criteria.

10 Claims, 12 Drawing Sheets

(56) References Cited

OTHER PUBLICATIONS

Sipkoff, M.; "Can Transparency Save Health Care?", *Managed Care Magazine*; Mar. 2004, obtained from http://www.managedcaremag.com/archives/0403/0403.transparency.html on Jul. 10, 2006.

Willis, Carla; "HSAs: More Than a (Tax) Shelter, Not Quite a House", *Virtual Mentor*. Ethics Journal of the American Medical Association, vol. 7, No. 7, Jul. 2005, obtained from http://www.ama-assn.org/amal/pub/upload/mm/384/oped4_0705.pdf on Jul. 10, 2006.

U.S. Appl. No. 12/563,911, filed Sep. 21, 2009, Medeiros et al.

Vanessa Fuhrmans, Wall Street Journal, "Insurer Reveals What Doctors Really Charge to Help People Compare Fees Aetna Posts . . . ," Aug. 18, 2005, obtained from the internet on Oct. 8, 2009 at http://www.myhealthcareadvisor.com/news/0050818-wsj (3 pages).

Aetna Inc., "We Want You to Know™," Aug. 22, 2005 (8 pages).

* cited by examiner

| Minor Procedures | |
|---|---|
| Procedure Description | Rate |
| External Cardioassist | $104.49 |
| Electronic Analysis Pacemaker (Two Chamber), with Recording & reprogramming | $44.87 |
| Telephone Analysis of Pacemaker (Two Chamber) | $39.34 |
| Telephone Analysis of Pacemaker (One Chamber) | $34.44 |
| Doppler Ultrasound of Arteries in the Head - Both Sides | $234.48 |
| Noninvasive Study of Upper Or Lower Extremity Arteries, single level | $110.29 |

707    710   Back to top

| Major Procedures | |
|---|---|
| Procedure Description | Rate |
| Injection for Coronary X-rays | $23.39 |
| Injection for Heart X-rays | $16.83 |
| Left Heart Catheterization | $1818.69 |
| Biopsy of Heart Lining | $345.59 |
| Right Heart Catheter | $884.97 |
| Injection for Aortography | $14.77 |

708    710   Back to top

| Other Services | |
|---|---|
| Procedure Description | Rate |
| Physician Services For Outpatient Cardiac Rehabilitation with Continuous EKG Monitoring | $28.70 |

Back to top

View average in and out of network costs for services in your area with Estimate the Cost of Care

IMPORTANT INFORMATION: This list includes the most common services billed by doctors with the listed primary specialty. The rates shown are those negotiated between Aetna and this doctor. These rates may change from time to time. These rates assume that a single unit of the service was provided, except where specifically noted. The rates only reflect the rates for the doctor's own services and not charges for additional services you may receive, such as anesthesia, pharmacy, medical supplies and facility charges. If your doctor has a capitated arrangement with Aetna, and the service received is considered covered under the capitation arrangement, these rates do not apply.

The appearance of a service on the rates page does not guarantee coverage for this service. All payments to doctors are subject to additional rules and guidelines, including Aetna's clinical and payment policies. These rates do not take into account the benefits and rules applicable to your plan of benefits, nor your own cost-sharing responsibility, such as copays, coinsurance, and deductibles. Doctor's rates are only one of many factors that you should consider when making health care decisions. We encourage you to discuss the information found on this site with your doctor.

THIS RATE INFORMATION IS SOLELY FOR USE BY AETNA MEMBERS FOR THE PURPOSE OF ALLOWING THEM TO EVALUATE THE COSTS FOR SERVICES PROVIDED BY A DOCTOR. ANY OTHER USE OF THIS INFORMATION IS STRICTLY PROHIBITED.

FIGURE 8

Aexcel Evaluation Standards

Provider Name: Anderson, Anthony, MD * Aexcel Designated Learn More
Specialty(ies): Cardiovascular Disease
Address: 151 Farmington Avenue, Hartford, CT 06156
Phone Number(s)(860) 273 XXXX This specialist was Aexcel-designated based on meeting the evaluation standards checked below. Learn more

What this information tells you: The information below was used to evaluate this specialist's performance, based on clinical quality and efficiency standards for the Aexcel designation.

How to use this information: The evaluation below should be viewed as an informational resource to assist you in making more informed health care decisions. You should always consult with your doctor about your health care decisions.

☑ Checked box indicates met standard

☑ Volume
 - This specialist saw enough Aetna members over the past two years to be evaluated for the Aexcel Designation.

☑ Clinical Quality
 - Adverse Event – when a complication or problem occurs.
 - 30-day readmission rate - unexpectedly re-admitted to the hospital within 30 days.
 - Use of beta blockers, ACE inhibitors and/or statin - use of medicines to treat patients with a history of heart attacks, heart disease or heart failure.

☑ Efficiency
 - A comparison of the resources used to treat health care events managed by this specialist as compared to resources used by other specialists in the same area and specialty.

Important Information: Even if a doctor has Aexcel designation or has met any of the standards checked above, there is no guarantee as to the quality of the service you receive from that doctor, or the outcome of any treatment by that doctor. Also, if a doctor is not designated for Aexcel or has not met a particular standard, this does not mean the doctor does not provide quality services. The Aexcel designation is one of many factors that you may consider when making health care decisions. We encourage you to discuss the information found on this site with your doctor.

FIGURE 11

PROVIDING TRANSPARENT HEALTH CARE INFORMATION TO CONSUMERS

FIELD OF THE INVENTION

This invention relates generally to the field of health insurance and more specifically to the area of price and information transparency for contracted health care providers.

BACKGROUND OF THE INVENTION

Imagine a world without price tags. A consumer can buy a big screen TV that he's had his eye on, but he would not know the price until his credit card bill came in the mail. Although this seems like a ridiculous proposition, it is exactly the world the average American lives in when he or she seeks medical care. As reported in the Wall Street Journal in February and June of 2005, knowing the cost of a doctor's visit has long been a missing piece of the health care decision-making process.

One previously unachievable approach is called "price transparency." Through price transparency, consumers would be able to know what they can expect to pay at the physician's office before visiting the physician. However, in previous health care systems, no health insurer has ever been able to provide this level of detail to its members. The reasons for this have been varied—contractual issues, complexities in the rates physicians agree to accept from insurers, and concerns about consumers shopping for health care on price alone.

BRIEF SUMMARY OF THE INVENTION

Embodiments of the invention provide consumers with online access to the negotiated discounted rates for health care procedures provided by primary care and specialist physicians. This provides advantages by educating consumers about the actual costs of medical care, responding to a need of the employer and broker communities. Such embodiments are particularly valuable in the face of the increased adoption of consumer-directed health plans, which necessitate more detailed information than had previously been available for health issues, health care quality, and average pricing within specific geographies.

Using embodiments of the invention, consumers can research what they can expect to pay at a doctor's office before going in for a visit. The research can be conducted securely via a password-protected interface to a query engine, such as a member website. The query engine can access information on health providers and health provider groups in conjunction with a health insurance company or other health plan organization. Members can search for a physician and, upon selecting a physician, can view negotiated contracted rates. This provides advantages to members who are selecting health care providers for services, and also to members who may be choosing health care benefits at the beginning of a plan year. By raising awareness about the costs of care, the marketplace for consumers as health care decision-makers is enhanced.

Embodiments of the invention provide information on overall value, not just price alone. Quality and efficiency measures are used and are in alignment with the Institute of Medicine's criteria for efficiency and effectiveness.

In one aspect, a method is provided for providing a health care consumer with information for a prospectively performed health service, the method comprising entering a contractual relationship with a health care provider to compensate the provider in a predetermined monetary amount for performing a health service for members of a health plan, providing an interface to the consumer through which consumer identity information can be entered, receiving the consumer identity information, determining that the consumer is a member of the health plan, and presenting, for the consumer, cost information for the prospectively performed health service, the cost information comprising the predetermined monetary amount and in accordance with the health plan.

In another aspect, a system is provided for use with a health plan organization offering a health care plan and a health care consumer subscribing to the health care plan, the system for providing the health care consumer with cost information for a first health service, the first health service providable by any of one or more health service providers in a collection of providers, each provider in the collection having a contractual relationship with the health plan organization, the system comprising a database containing cost information for health services provided by one or more providers in the collection, the cost information comprising the amount the provider will charge for rendering health services under the contractual relationship, query specifying means for specifying query criteria to be queried of the database, query receiving means for receiving query criteria and for querying the database, and presentation means for presenting to the consumer cost information for the first health service, said cost information obtained from the database according to the specified query criteria and according to the consumer's subscription to the health care plan.

In yet another aspect, a method is provided for obtaining information for a health care service prospectively to be rendered by a health care provider, the health care provider under a contractual relationship with a health plan organization, the method comprising transmitting consumer identity information, the identity information corresponding to a health care plan offered by the health plan organization, specifying, via a user interface, query criteria for provider-related information, transmitting a query comprising the specified criteria to a database for the health plan organization, receiving, from the database and in response to the query, information relating to the health care provider, the information comprising a monetary amount for which the health care provider would be compensated for performing the health service according to the consumer's health plan and under the contractual relationship.

BRIEF DESCRIPTION OF THE DRAWINGS

While the appended claims set forth the features of the present invention with particularity, the invention and its advantages are best understood from the following detailed description taken in conjunction with the accompanying drawings, of which:

FIGS. 2-8 are screenshots illustrating exemplary user interfaces for presenting health care provider information, in accordance with an embodiment of the invention;

FIG. 11 is an exemplary presentation of quality and efficiency information for a provider, in accordance with an embodiment of the invention.

DETAILED DESCRIPTION OF THE INVENTION

The following examples further illustrate the invention but, of course, should not be construed as in any way limiting its scope.

Figure 1:
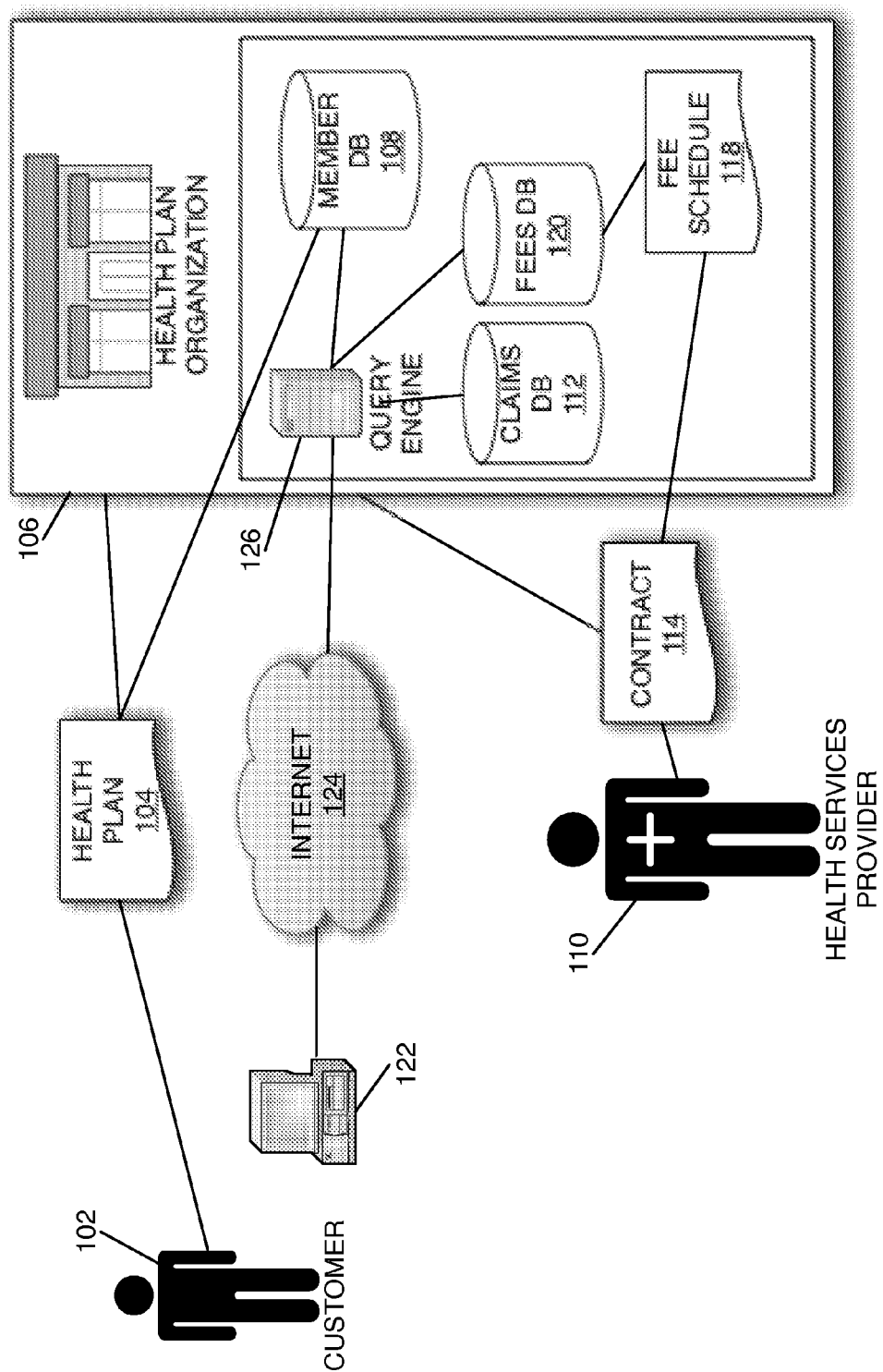
FIG. 1 is a diagram of a system used to provide health care provider information to consumers, in accordance with an embodiment of the invention.

Turning to FIG. 1, an implementation of a system contemplated by an embodiment of the invention is shown with reference to an overall healthcare environment. A consumer ("subscriber" or "member") 102 is a member of a health plan 104 of a health plan organization ("HPO") 106. Alternatively, the consumer 102 is a prospective member of a health plan 104. The member 102 may subscribe to the health plan 104 through, for example, his employer. Alternatively, the member 102 may obtain benefits of the health plan 104 through a subscriber (e.g., a spouse or child of a subscriber can be a member of a health plan). The HPO 106 is typically a health insurance company and the health plan 104 can be one of a number of health insurance or related products, such as a PPO, HMO, POS, or the like. The health plan 104 can also be a consumer-directed health plan, such as a high deductible health plan, health reimbursement arrangement (HRA), health savings account (HSA) or the like. The member's 102 plan 104 covers various health care services according to one of a variety of pre-arranged terms, and details for the member 102 and the corresponding plan 104 are preferably stored in a member database 108. The terms of the plan 104 can vary greatly from plan to plan according to: what types of services are provided, where the services are provided, by whom they are provided, the extent to which the patient is personally responsible for payment, amount of deductibles, etc. Generally, however, regardless of the specific plan subscribed to, when a member 102 obtains health care services from a provider 110, either the patient 102 or the provider 110 can submit a claim to the HPO 106 for reimbursement or payment. For analysis purposes, historical claim data is stored in a claims database 112.

A health care services provider 110 may have a contractual relationship 114 with the HPO 106. Under the contract 114, the provider 110 typically agrees to provide services to members 102 of the HPO 106 at scheduled rates. The rates are stored in a fee schedule 118, preferably stored in a fees database 120 maintained by the HPO 106. By contracting with the HPO 106, the provider 110 generally increases the amount of business he receives from members 102, and members 102 generally receive a less expensive rate than they would otherwise receive for a health service provided by the provider 110, and at least a portion of the provider's 110 compensation is generally paid by the HPO 106. The actual amount of out-of-pocket expense to be paid by a member 102 may vary according to the terms of his health plan 104 (e.g., co-payments, co-insurance or deductibles may apply), but will generally be at most the contracted rate. Historically, these contracted rates have been guarded fairly closely by HPOs 106. Consumers often would not become aware of their charges until after they were billed for past services. Moreover, different contracted providers may operate on different fee schedules for the same health services without any knowledge by the consumer.

In an embodiment of the invention, consumers 102 can obtain cost information and other relevant data (quality information, efficiency information, etc.) prior to the provision of any health services by a provider 110. The consumer 102 uses a computing device 122 to communicate via a network, such as the Internet 124, with the HPO 106. An interface is preferably provided so the consumer 102 can identify himself as a member of a health plan 104 of the HPO 106, and so the consumer 102 can research information on providers 110 who prospectively may perform health services for the consumer 102. Through the interface, a query is sent to a query engine 126. The query engine 126 connects to one or more databases of the HPO and obtains price information, provider quality information, provider efficiency information, or other information that may be useful to the consumer's 102 deciding on a provider of health services.

Figure 2:
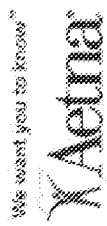
Figure 3:
Figure 4:
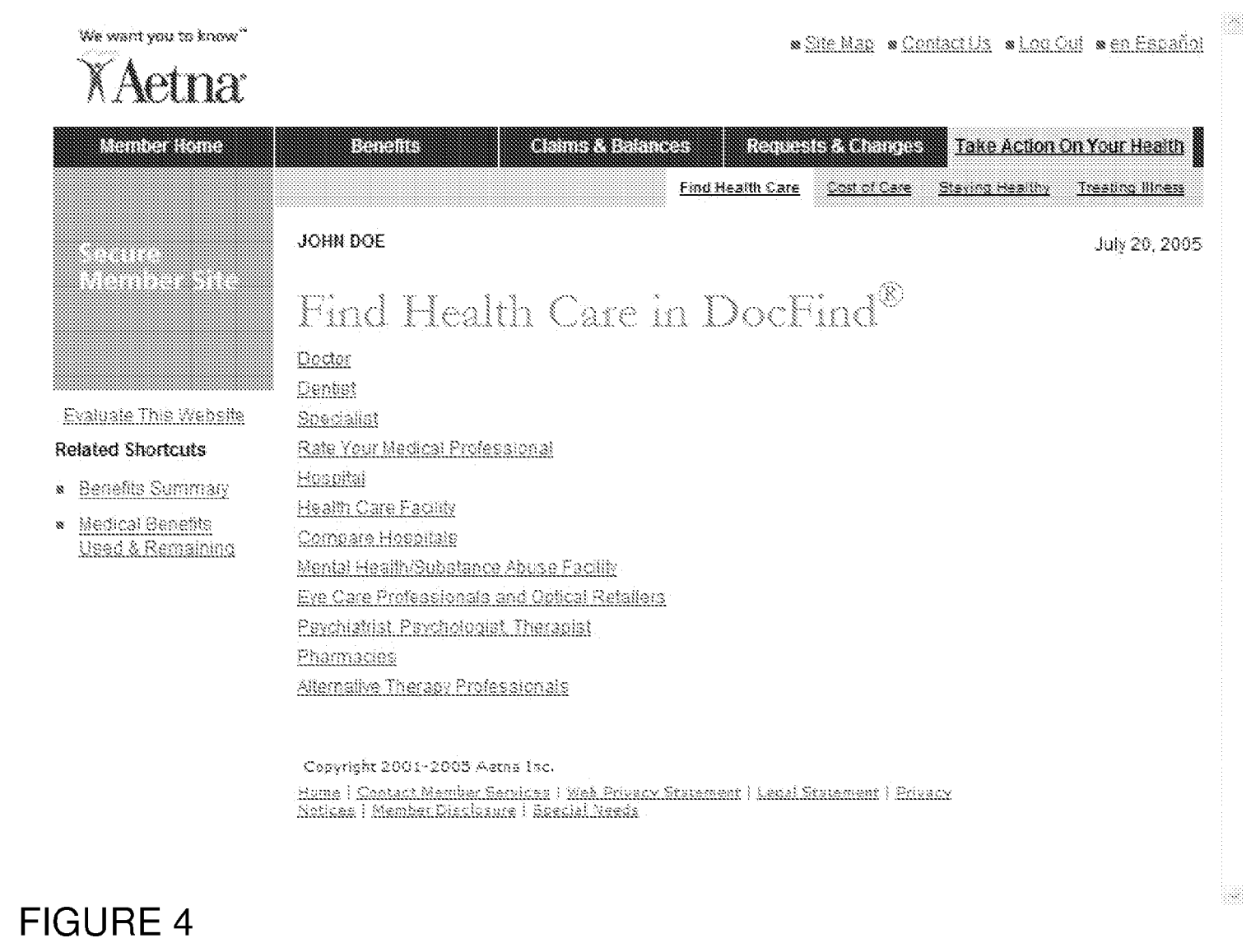
Figure 6:

FIGS. 2-8 illustrate a sample interface provided by an HPO for presenting health care provider information, as used in an embodiment of the invention. In FIG. 2, a login screen 202 is shown whereby a member can enter a username 204 and password 206 in order to obtain access to the system. Alternatively, or in addition, non-members can access the system under particular circumstances. In FIG. 3, basic member information is presented as obtained, for example, from member and/or claims databases. Also presented in the screen of FIG. 3 is an option to find health care providers 302. By selecting this option, a member is presented with another screen as shown in FIG. 4, where the member can choose the type of health service provider or facility for which he would like more information.

Figure 5:
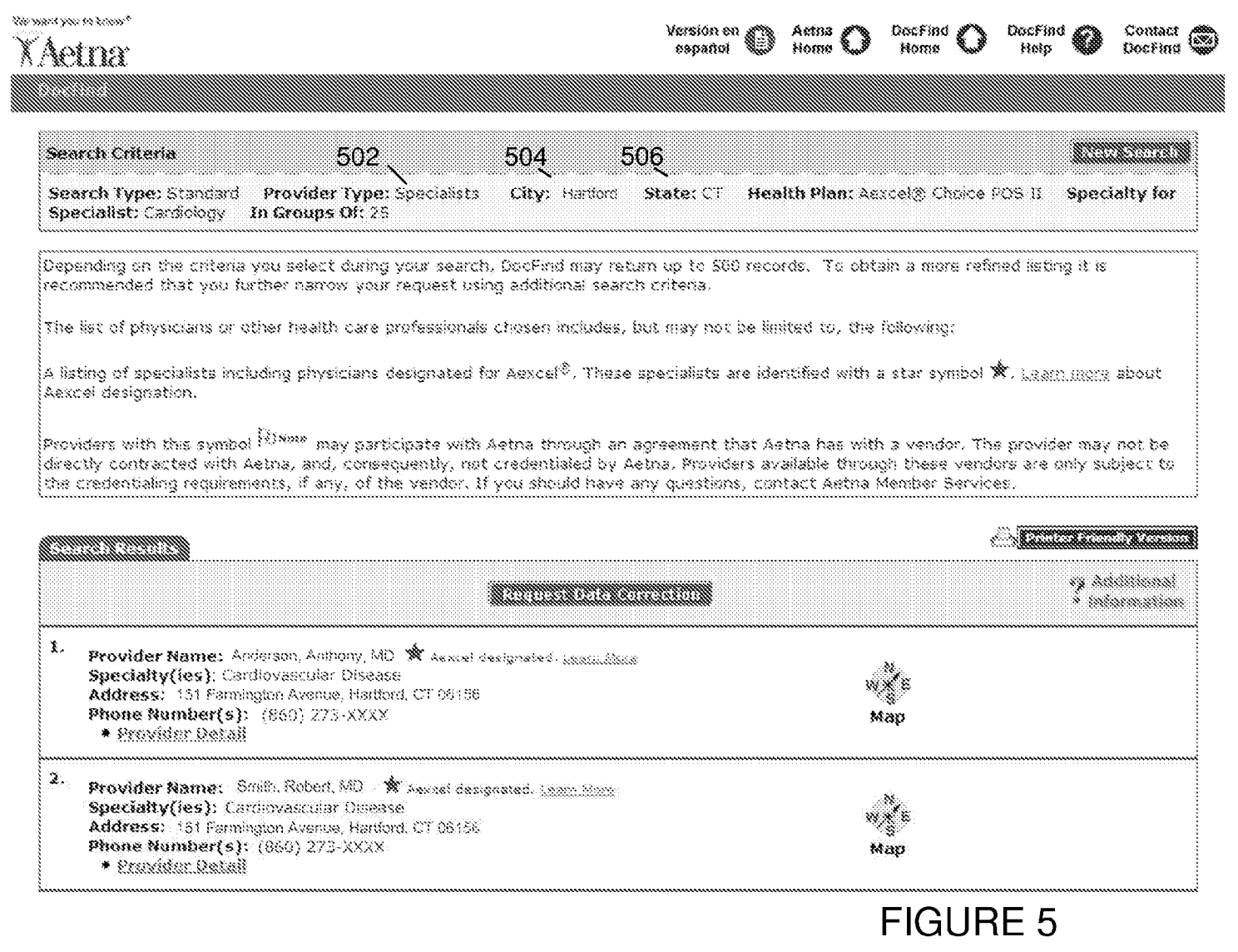

FIG. 5 illustrates the results of a query where the member has requested information on "Specialists" 502 within a city 504 and state 506. Other search criteria, (e.g., providers within a twenty mile radius of a specified zip code) are also available. Basic information (e.g., name, specialty, address and phone numbers) for contracted health services providers matching the query criteria are presented in response to the query. Additionally, an option 508 is presented for obtaining additional details on particular providers. These additional details are provided in a screen such as the one shown in FIG. 6, and preferably include details such as the provider's education, hospital affiliations, gender, or other information that may be of value to consumers. An option 602 is further presented to view the provider's contracted rates for provision of services to HPO members. An option 604 is presented to view the provider's quality and efficiency information.

Figure 7:

When the option 602 is selected, the member is preferably presented with one or more screens such as those shown in FIGS. 7-8. The screens contain one or more tables 702, 704, 706, 708. Each table contains a group of categorized procedures, such as Office Visits 702, Diagnostic Services 704, Minor Procedures 706, Major Procedures 707 (births, Caesarean sections, shoulder surgery, multiple bypass surgery, cadiology procedures, etc.), or Other Services 708. The procedures displayed are preferably unique to the given specialty of the provider, so that the procedures displayed for a cardiologist will differ from the procedures displayed for a pediatrician, for example. For each procedure in a table, a rate 710 is shown. The rate 710 represents the amount that the provider will be reimbursed for performing the corresponding procedure. Depending on the member's health plan, he may pay less for these services if any portion is to be paid by the HPO. The invention is not limited to the interface as shown in FIGS. 7 and 8, however. In some embodiments of the invention, the actual amount to be paid by the member is presented. In some embodiments, only a selection of possible procedures are presented via the interface (e.g., the 30 most frequently performed). The determination of which procedures are to be presented can be made by a preferably quantitative procedure, such as examining which procedure codes (CPT) appear most frequently on previously submitted claims for the specialty.

Figure 9:
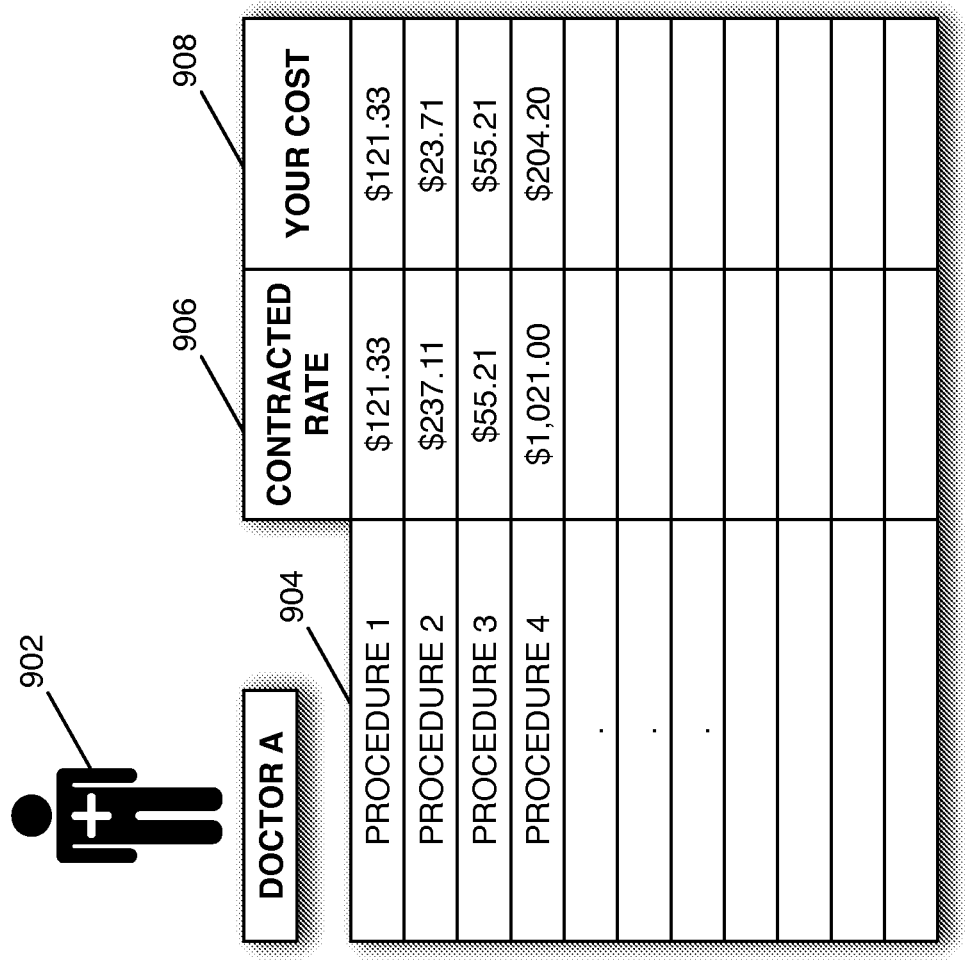
FIG. 9 is an exemplary presentation of price information for a health care provider, in accordance with an embodiment of the invention.

Turning to FIG. 9, an exemplary screen is shown whereby a member can obtain cost information for a contracted health services provider 902, in accordance with an embodiment of the invention. As in FIGS. 7 and 8, a variety of health service procedures performable by the provider 902 are listed in one column 904. The listed procedures in the column 904 are preferably presented in a nomenclature easily understandable to a layman, which may differ from an actual formal description associated with a procedure's CPT code. A second column 906 contains the negotiated contracted rate the provider will be reimbursed for performing the procedure. A third column 908 contains the actual cost the member would pay for having the service performed by this provider. This actual cost can differ from the contracted rate due to terms of the member's health plan, which can be stored in one of the HPO's databases. Differences may result from coinsurance, co-payments, satisfaction of deductibles, etc.

Figure 10:
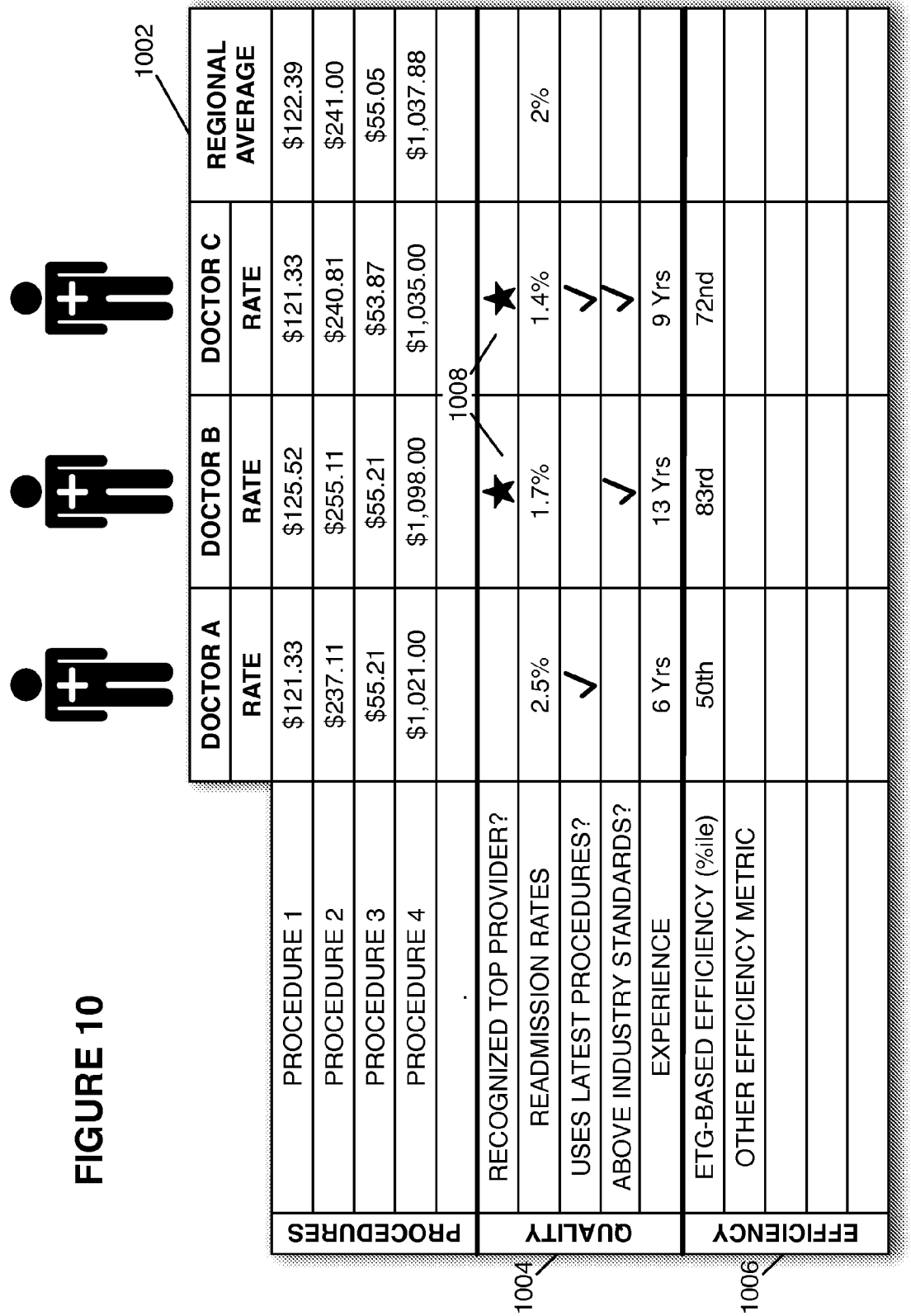
FIG. 10 is an exemplary presentation of comparative data between health care providers, in accordance with an embodiment of the invention.

In some embodiments of the invention, comparative information is provided for multiple health service providers, as illustrated in FIG. 10. In addition to the columns previously described with respect to FIGS. 8 and 9, multiple columns are presented for multiple health service providers to allow for side-by-side comparison with respect to given procedures. For example, the contracted rate for a procedure to be performed by Doctor A may be less than the contracted rate for the same procedure when performed by Doctor B. Such a direct comparison and revelation of contracted rates has not been available in previous systems. In some embodiments of the invention, the comparative information in the table is sortable by selected criteria, which is particularly useful if a number of providers are being simultaneously compared.

In addition, a column 1002 is shown to provide a regional average contracted rate for a given procedure, as used in some embodiments of the invention. The regional average can be calculated for the member based on a location specified in a query, or based on his customer information stored in an HPO database. In some embodiments, the size of the region can be customized on a query-by-query basis (e.g., "within 10 miles"), or based on zip code, or other geographic identifier.

Also shown in FIG. 10 are additional evaluation criteria that may be useful to consumers making health care decisions. Such criteria include quality metrics 1004 and efficiency metrics 1006. The quality metrics 1004 can include, for example, whether a health services provider has been recognized as an outstanding provider. Doctors B and C in FIG. 10 are shown in the example to be outstanding providers by the stars 1008 in their respective table cells. The recognition can come from the HPO based on internal or external metrics, or from outside parties such as certifying agencies like AQA (Ambulatory Care Quality Alliance) or The Leapfrog Group.

Another of the quality metrics 1004 is the rate of readmission of a provider's patients for similar treatments. A lower readmission rate may indicate to a prospective patient that one provider provides a higher quality of care than another. A period of time may be used (e.g., 30 days) to determine if patients have been readmitted. Similarly, information regarding the number or frequency of adverse effects in patients of the provider can be used as a quality metric. Another of the quality metrics 1004 is whether a provider uses the latest health care procedures, or performs according to or in excess of industry standards. For example, one metric can be whether an Ob/Gyn screens for cervical cancer, or performs HIV tests, during routine examinations. Data for such metrics can be obtained, for example, from past claim data submitted with respect to the particular provider. Additionally, other metrics can be used as proxies for quality, such as the number of years of experience a provider has, the volume of the number of patients using the provider, or the volume of the services performed by the provider. In some embodiments of the invention, survey data is included as a quality metric, such as from a patient satisfaction survey or an industry peer survey.

Efficiency metrics 1006 can also be used and presented to the member. Efficiency can measure, for instance, the total cost for treatment of a particular medical condition. Because the treatment may comprise multiple procedures and other expenses (pharmaceutical, lab, hospitalization, etc.), such an efficiency metric for a given provider can be of greater value to a prospective patient than the costs of individual procedures, since the sum total of all expected health care costs for that patient may be less with one provider who is more efficient than another. Efficiency metrics can be evaluated using past claim data submitted with respect to providers. Claim data generally contains "procedure codes" and "diagnosis codes". Claims can thus be grouped into episodes of treatment, or ETGs ("episode treatment groups"), which can further be associated into particular health conditions. By aggregating the costs of claims within ETGs or conditions, efficiency metrics can be computed and compared across providers.

An additional example of a presentation of quality and efficiency information to prospective consumers of a health care provider is shown in FIG. 11.

In some embodiments of the invention, cost information is provided not only for individual procedures, but for all anticipated costs associated with a procedure. For example, a prospective patient investigating the cost of having an outpatient surgery is presented not only with the contracted rate from the physician, but with contracted rates for the hospital or clinic where the surgery is to be performed, an anesthesiologist who may be required, associated laboratory fees for required testing, and the like. In some embodiments, expected pharmaceutical costs are also included. Such a "soup-to-nuts" pricing estimate may be of tremendous value to prospective patients of elective or planned surgeries, and can make use of existing evaluation tools that may exist or be developed for individual components (e.g., tools for comparing hospital costs). Additionally, in some embodiments of the invention, prospective patients are presented with contracted rates for a health service to be provided at one or more particular sites of service. In this way, a prospective patient can compare the cost of having a procedure performed at one site (e.g., a hospital) versus another site (e.g., an outpatient clinic).

Figure 12:
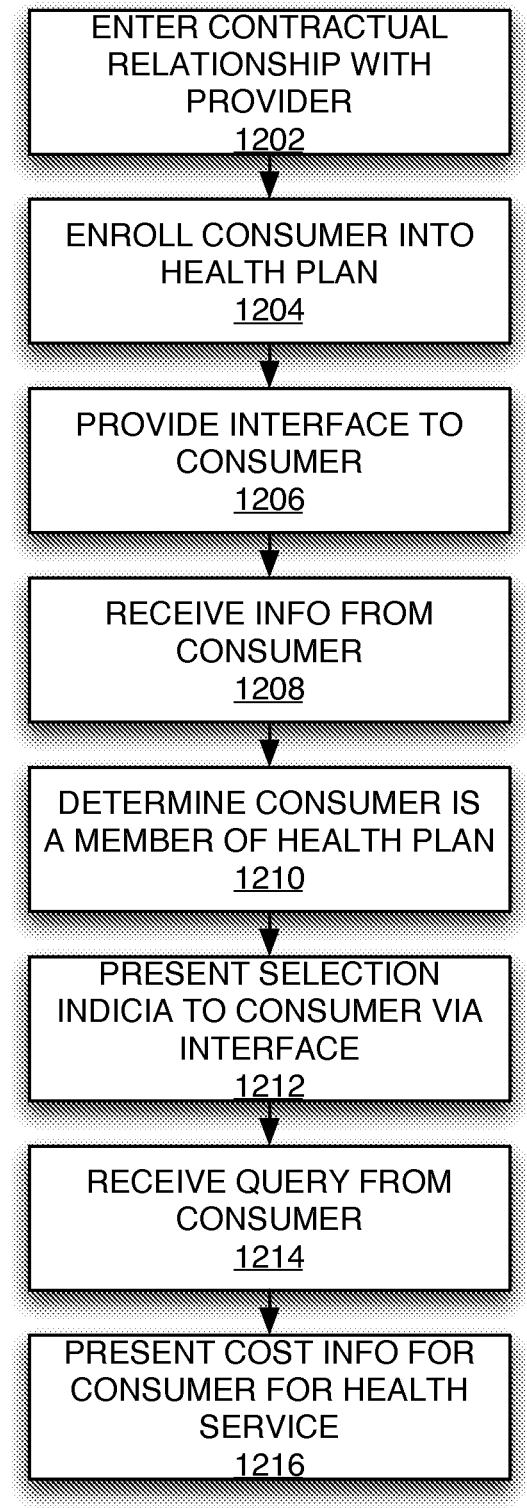
FIG. 12 is a flow diagram of a technique for presenting health care cost information to a consumer, in accordance with an embodiment of the invention.

Turning to FIG. 12, a method is shown for providing cost information to a prospective consumer of health services, in accordance with an embodiment of the invention. A health plan organization (HPO) enters a contractual relationship with a health services provider at step 1202. The contract sets a schedule of rates for which the provider is reimbursed for providing services to patients who are members of the HPO. The HPO enrolls a consumer as a member of one of its offered health plans at step 1204 and provides him an interface at step 1206. At step 1208, the HPO receives information from the consumer (e.g., a username and password) and determines that the consumer is a member of a health plan offered by the HPO at step 1210. The consumer is presented, through the interface, with a selection options for querying about provider and/or procedure data at step 1212. The query is received at step 1214 and, in response, cost information is presented to the consumer at step 1216.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for providing a health care consumer with information for a prospectively performed health service for treatment of at least one health condition, the method comprising:
    providing an electronic health care user interface to the consumer through which consumer identity information can be entered;
    receiving the consumer identity information from the electronic health care user interface;
    determining, by a health care computer system, that the consumer is a member of a health insurance plan provided by a health plan organization;
    receiving, by the electronic health care user interface, a selection by the consumer of a first health care provider, wherein the first health care provider has a contractual relationship with the health plan organization that specifies a first monetary amount that the first health care provider would charge for rendering the health service and/or a second monetary amount that the first health care provider would be compensated by the health plan organization for rendering the health service;
    determining, by the health care computer system, a treatment cost efficiency metric for the first health care provider based on a total cost of treatment of the at least one health condition rendered by the first health care provider, including:
        grouping health insurance plan claim data for the first health care provider into an episode treatment group based on at least one of procedure codes and diagnosis codes associated with the claim data for the first health care provider;
        associating the claim data in the episode treatment group with the at least one health condition;
        aggregating costs for the claim data within the episode treatment group for measuring the total cost of treatment from the first health care provider of the at least one health condition; and
        calculating the treatment cost efficiency metric for the first health care provider as a percentile ranking among a plurality of health care providers of the total cost of treatment of the at least one health condition;
    presenting, to the consumer, by the electronic health care user interface, cost information for performing the health service and the treatment cost efficiency metric for the first health care provider, wherein the cost information is based on the first monetary amount and/or the second monetary amount under the contractual relationship and in accordance with the health insurance plan, and wherein the cost information and the treatment cost efficiency metric are presented to the consumer prior to the first health care provider performing the health service;
    presenting, to the consumer, by the electronic health care user interface, quality information for the first health care provider, wherein the quality information includes indicia for each of: compliance of the first health care provider with predetermined quality criteria, a frequency of adverse reactions in past patients of the first health care provider, rates that past patients of the first health care provider subsequently have sought similar health care services, an indication of whether the first health care provider uses latest procedure, and comparison of the indicia to industry standards; and
    receiving, by the health care computer system, cost information and quality information relating to a second health care provider, the second health care provider also under a contractual relationship with the health plan organization, wherein the received cost information and quality information for the health care provider and the second health care provider are presented by the electronic health care user interface in a comparative arrangement.

2. The method of claim 1 wherein the health plan is a consumer-directed health plan.

3. The method of claim 2 wherein the health plan is a high deductible health plan.

4. The method of claim 1 wherein the first and second health care providers are within a specified geographic proximity to the consumer.

5. The method of claim 1 further comprising:
    entering a plurality of contractual relationships with a plurality of health care providers to compensate the providers in predetermined monetary amounts for performing the health service for members of the health plan, each provider in the plurality being located within a specified geographic proximity to the consumer; and
    wherein the cost information further comprises a mathematical function of the predetermined monetary amounts.

6. The method of claim 1 further comprising presenting to the consumer, via the electronic health care user interface, a list of health services determined to be provided with high frequency by the first health care provider.

7. The method of claim 1 wherein the health service is a member of the group consisting of: delivery of baby; Caesarian section; shoulder surgery; and heart surgery.

8. The method of claim 1 further comprising comparing the efficiency metric to industry standards.

9. A method of obtaining information for a health care service prospectively to be rendered by a health care provider for treatment of at least one health condition, the method comprising:
- transmitting, via a network, consumer identity information, the identity information corresponding to a health care insurance plan offered by a health plan organization;
- specifying, via an electronic user interface of a first computer system, query criteria for provider-related information including a selection of the health care provider, wherein the health care provider has a contractual relationship with the health plan organization that specifies a first monetary amount that the health care provider would charge for rendering the health service and/or a second monetary amount that the health care provider would be compensated by the health plan organization for rendering the health service;
- transmitting, by the first computer system, a query comprising the specified criteria to a computer database system for the health plan organization;
- determining, by the first computer system, a treatment cost efficiency metric for the health care provider corresponding to the selection based on a total cost of treatment of the at least one health condition by the health care provider rendering a health care service, including:
  - grouping health care insurance plan claim data for the health care provider into an episode treatment group based on at least one of procedure codes and diagnosis codes associated with the claim data for the health care provider;
  - associating the claim data in the episode treatment group with the at least one health condition;
  - aggregating costs for the claim data within the episode treatment group for measuring the total cost of treatment from the health care provider of the at least one health condition; and
  - calculating the treatment cost efficiency metric for the health care provider corresponding to the selection as a percentile ranking among a plurality of health care providers of the total cost of treatment of the at least one health condition;
- receiving, from the computer database system and in response to the query, information relating to the health care provider, the information comprising the treatment cost efficiency metric for the health care provider, cost information, and quality information, wherein the cost information is based on the first monetary amount and/or the second monetary amount under the contractual relationship and in accordance with the health insurance plan, and wherein the cost information and the treatment cost efficiency metric are received from the computer database system prior to the first health care provider performing the health service;
- presenting, via an electronic user interface, cost information and quality information for the health care provider, wherein the quality information includes indicia for each of: compliance of the health care provider with predetermined quality criteria, a frequency of adverse reactions in past patients of the health care provider, rates that past patients of the health care provider subsequently have sought similar health care services, an indication of whether the first health care provider uses latest procedure, and comparison of the indicia to industry standards; and
- receiving, from the computer database system, cost information and quality information relating to a second health care provider, the second health care provider also under a contractual relationship with the health plan organization, wherein the received cost information and quality information for the health care provider and the second health care provider are presented in a comparative arrangement.

10. A system for obtaining information for a health care service prospectively to be rendered by a health care provider for treatment of at least one health condition, the system comprising:
- a computer database system for a health plan organization including cost information for health services provided by one or more health care providers in a collection of providers, the cost information comprising a first monetary amount that the one or more providers would charge for rendering health services and/or a second monetary amount that the one or more providers would be compensated by the health plan organization for rendering the health services;
- a computer processor; and
- a computer readable medium having stored thereon computer executable instructions that, when executed by the computer processer, cause for:
  - transmitting, via a network, consumer identity information, the identity information corresponding to a health care insurance plan offered by the health plan organization;
  - specifying, via an electronic user interface, query criteria for provider-related information including a selection of the health care provider;
  - transmitting a query comprising the specified criteria to the computer database system for the health plan organization;
  - determining a treatment cost efficiency metric for the health care provider corresponding to the selection based on a total cost of treatment of the at least one health condition by the health care provider rendering a health care service, including:
    - grouping health care insurance plan claim data for the health care provider into an episode treatment group based on at least one of procedure codes and diagnosis codes associated with the claim data for the health care provider;
    - associating the claim data in the episode treatment group with the at least one health condition;
    - aggregating costs for the claim data within the episode treatment group for measuring the total cost of treatment from the health care provider of the at least one health condition; and
    - calculating the treatment cost efficiency metric for the health care provider corresponding to the selection as a percentile ranking among a plurality of health care providers of the total cost of treatment of the at least one health condition;
  - receiving, from the computer database system and in response to the query, information relating to the health care provider, the information comprising the treatment cost efficiency metric for the health care provider, cost information, and quality information, wherein the cost information is based on the first monetary amount and/or the second monetary amount under the contractual relationship and in accordance with the health insurance plan, and wherein the cost information and the treatment cost efficiency metric are received from the computer database system prior to the first health care provider performing the health service;

presenting the cost information and the quality information for the health care provider, wherein the quality information includes indicia for each of:

compliance of the health care provider with predetermined quality criteria, a frequency of adverse reactions in past patients of the health care provider, rates that past patients of the health care provider subsequently have sought similar health care services, an indication of whether the first health care provider uses latest procedure, and comparison of the indicia to industry standards; and receiving, from the computer database system, cost information and quality information relating to a second health care provider, the second health care provider also under a contractual relationship with the health plan organization, wherein the received cost information and quality information for the health care provider and the second health care provider are presented in a comparative arrangement.

* * * * *